United States Patent
Webler, Jr.

(10) Patent No.: US 6,682,553 B1
(45) Date of Patent: Jan. 27, 2004

(54) SYSTEM AND METHOD FOR STENT RETENTION

(75) Inventor: William E. Webler, Jr., Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 217 days.

(21) Appl. No.: 09/753,225

(22) Filed: Dec. 28, 2000

(51) Int. Cl.⁷ .................................................. A61F 2/06
(52) U.S. Cl. ...................................... 623/1.11; 623/1.12
(58) Field of Search ............................... 623/1.1, 1.11, 623/1.13, 1.23, 1.39–1.48

(56) References Cited

U.S. PATENT DOCUMENTS

| | | | |
|---|---|---|---|
| 4,702,252 A | * 10/1987 | Brooks et al. | 606/195 |
| 4,733,665 A | 3/1988 | Palmaz | |
| 5,108,416 A | 4/1992 | Ryan et al. | |
| 5,158,548 A | 10/1992 | Lau et al. | |
| 5,242,399 A | 9/1993 | Lau et al. | |
| 5,344,426 A | 9/1994 | Lau et al. | |
| 5,807,327 A | * 9/1998 | Green et al. | 623/1.11 |
| 5,830,217 A | 11/1998 | Ryan | |
| 5,836,965 A | 11/1998 | Jendersee et al. | |
| 5,968,091 A | * 10/1999 | Pinchuk et al. | 623/1.16 |
| 5,976,155 A | 11/1999 | Foreman et al. | |
| 6,335,029 B1 | * 1/2002 | Kamath et al. | 424/423 |
| 6,348,060 B1 | 2/2002 | Brown | |

* cited by examiner

Primary Examiner—Corrine McDermott
Assistant Examiner—Hieu Phan
(74) Attorney, Agent, or Firm—Fulwider Patton Lee & Utecht, LLP

(57) ABSTRACT

The system and method for retaining a stent on an expandable stent delivery member involves applying a plastic material that will adhere or fuse to the expandable stent delivery member, and that is insoluble in blood, to one or both of the expandable stent delivery member and the stent, and mounting the stent over the expandable stent delivery member. The plastic material may be dissolved in a solvent to form a dispersion, and applied to the expandable stent delivery member and/or the stent, and is allowed to evaporate to deposit the plastic material. The plastic material also may be applied after the stent is mounted on the expandable stent delivery member, as a coating, or may be applied as knobs or fillets onto the expandable stent delivery member through the openings of the stent. Alternatively, a plastic material may be melted, applied as knobs or fillets onto the expandable stent delivery member through the openings of the stent, and allowed to cool, to retain the stent on the expandable stent delivery member. A system is also provided for applying a melted plastic material on an expandable stent delivery member for retaining a stent on the expandable stent delivery member.

18 Claims, 3 Drawing Sheets

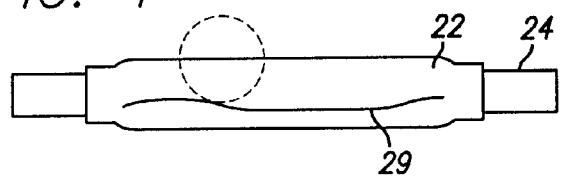
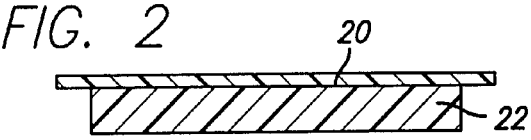
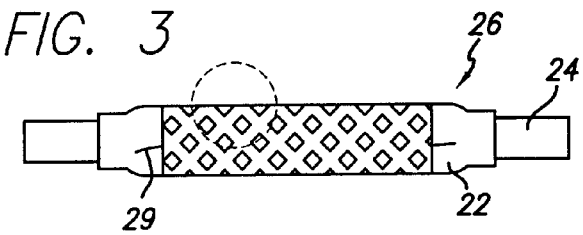
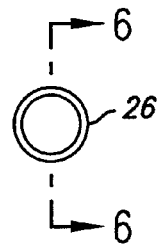
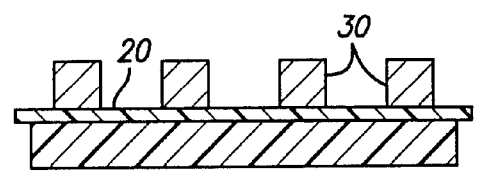
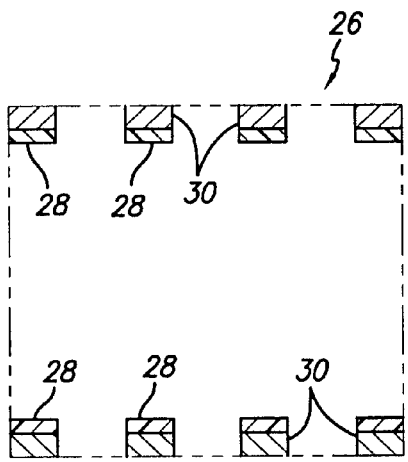
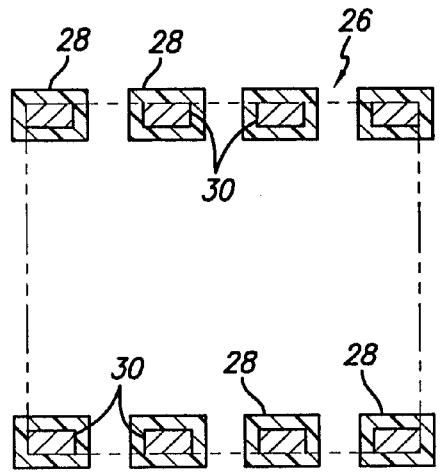

SYSTEM AND METHOD FOR STENT RETENTION

BACKGROUND OF THE INVENTION

1. Field of the Invention

This invention relates to expandable endoprosthesis devices, generally called stents, which are adapted to be implanted into a patient's body lumen, such as blood vessel, to maintain the patency thereof. These devices are very useful in the treatment of atherosclerotic stenosis in blood vessels. The invention more particularly relates to a method for increasing the stent retention properties of a stent delivery system.

2. Description of Related Art

Stents are generally tubular-shaped devices which function to hold open a segment of a blood vessel or other anatomical lumen. They are particularly suitable for use to support and hold back a dissected arterial lining which can occlude the fluid passageway therethrough.

Various means have been described to deliver and implant stents. One method frequently described for delivering a stent to a desired intraluminal location includes mounting the expandable stent on an expandable stent delivery member, such as a balloon, provided on the distal end of an intravascular catheter, advancing the catheter to the desired location within the patient's body lumen, inflating the expandable stent delivery member on the catheter to expand the stent into a permanent expanded condition and then deflating the expandable stent delivery member and removing the catheter. One of the difficulties encountered using prior stent delivery systems involved retaining the stent on the expandable stent delivery member during delivery of the stent to the desired location within the patient's body lumen, while at the same time maintaining the ability of the expandable stent delivery member to release the stent when desired, and maintaining sufficient longitudinal flexibility of the stent to facilitate its delivery.

Currently, stents are commonly mounted over a stent delivery balloon by placing a stent over a folded stent delivery balloon, placing the assembly in a tube or similar device to prevent the stent from expanding while the stent delivery balloon is pressurized, applying heat to the assembly, and pressurizing the stent delivery balloon. This causes the stent delivery balloon to expand somewhat between the struts of the stent, resulting in inclined areas of the stent delivery balloon to provide mechanical interference retaining the stent on the stent delivery balloon. A current trend is to design stents that are thinner and that have a smaller outer diameter, while still providing as much surface area as possible to provide scaffolding to a stenosis of a vessel. As a result, in more advanced thinner stent designs, the amount of mechanical interference provided by mounting of the stent on a stent delivery balloon in this manner is reduced. Also, once the stent moves out of the set position on the stent delivery balloon, retention forces decrease significantly, because the raised regions of the stent delivery balloon no longer match the pattern of the stent struts, and the mechanical interference of the raised, inclined areas of the stent delivery balloon is largely lost. The coefficient of friction of commonly used balloon materials such as nylons, polyethylene terephthalate, polyethylene, and the like, is typically not very high, and stent struts are typically polished or rounded, so that once the stent is displaced even slightly from the set position on the stent delivery balloon, the forces retaining the stent on the stent delivery balloon are greatly reduced.

One prior art stent delivery system provides for retention of a stent on a balloon by a capsule of material that slowly dissolves in blood. However, encapsulation of a stent can interfere with the release of the stent upon inflation of the balloon, can unacceptably increase the stent implantation procedure time due to the time required for the capsule of material to dissolve, and can reduce flexibility of the combination of the stent and the stent delivery balloon. The dissolving of an encapsulating material within the bloodstream can further release particles large enough to block blood flow downstream in the arterioles or capillary bed, and can contribute to thrombogenesis.

What has been needed and heretofore unavailable is a system and method for retaining a stent on an expandable stent delivery member that allows an assembly of a stent and a stent delivery system to maintain a high degree of flexibility, that allows the stent to be readily expanded and released when desired, and that does not utilize material that dissolves in the blood. The present invention addresses these and other needs.

SUMMARY OF THE INVENTION

Briefly, and in general terms, the present invention provides for retention of a stent on a stent delivery member without compromising the high degree of flexibility of the stent and stent delivery system needed to allow them to be advanced through the tortuous passageways of the vasculature, allowing the stent to be readily expanded and released when desired, allowing the stent to have the mechanical strength to hold open the body lumen into which it is expanded, and without contributing to thrombogenesis.

The present invention accordingly provides for a method for retaining a stent on an expandable stent delivery member, comprising the steps of applying a plastic material that is insoluble in blood to at least one of the expandable stent delivery member and the stent, and mounting the stent over the expandable stent delivery member. The plastic material will preferably adhere or fuse to the expandable stent delivery member. In another presently preferred aspect, the plastic material has a relatively high coefficient of friction. In a presently preferred embodiment, the expandable stent delivery member is an inflatable balloon member. The plastic material may be chosen from plastics, organic materials, resins, two part resins, polymers, copolymers, and combinations thereof. In a presently preferred embodiment the plastic material is chosen from ethylene acrylic acid (EAA) copolymers, polyvinyl chloride (PVC), ethylene vinyl acetate copolymer (EVA), ethylene glycol butyl ether acetate (EBA) and ethylene methyl acrylate (EMA) ethylene acrylic ester copolymers, ethylene acrylic ester maleic anhydride terpolymers, and acid copolymer resins. The plastic material may also incorporate a therapeutic agent, such as a compatible anti-thrombus agent, a drug for reducing the likelihood of clots forming on the stent and the stent delivery member during exposure of the stent and the stent delivery member to blood, an anti-restenosis agent, and combinations thereof. The plastic material may also advantageously include a cross-linking agent chosen from cross-linking catalysts and resins.

In order to improve the retention of the stent on the expandable stent delivery member, heat can be applied to the stent mounted over the expandable stent delivery member to enhance cross-linking of the plastic material. In an alternate approach, the step of mounting the stent over the expandable stent delivery member comprises disposing the stent on the expandable stent delivery member, and applying heat and pressure to the stent and the expandable stent delivery member to create an adhesive bond between the stent and the expandable stent delivery member. In a presently preferred embodiment, the plastic material will adhere to the expandable stent delivery member, and the surface of the expandable stent delivery member may also be etched prior to the step of applying the plastic material, to improve adherence of the plastic material to the expandable stent delivery member. Areas of the expandable stent delivery member may be masked prior to etching the surface of the expandable stent delivery member. In another aspect, a release agent may optionally be applied to one or both of the stent and the expandable stent delivery member prior to the step of mounting the stent over the expandable stent delivery member.

In a presently preferred embodiment, the step of applying the plastic material comprises dissolving the plastic material in a solvent to form a dispersion, and applying the dispersion of the plastic material to the expandable stent delivery member. In a presently preferred aspect, the expandable stent delivery member is folded prior to the step of applying the dispersion of the plastic material on the expandable stent delivery member. After the dispersion is applied to the expandable stent delivery member, the solvent is preferably evaporated from the dispersion of the plastic material on the expandable stent delivery member to deposit the plastic material on the expandable stent delivery member. In another alternate approach, the step of applying the plastic material comprises dissolving the plastic material in a solvent to form a dispersion, mounting the stent on the expandable stent delivery member, and applying the dispersion of the plastic material on the expandable stent delivery member and the stent to form a thin coating of the dispersion of the plastic material on the expandable stent delivery member and the stent. The dilution of the dispersion of the dissolved plastic material in the solvent can be adjusted to control the thickness of the coating that is deposited, and preferably the dilution of the dispersion is adjusted to be sufficiently thin so as to not significantly interfere with subsequent inflation of the expandable stent delivery member and deployment of the stent. Alternatively, the plastic material may be applied by applying the plastic material by plasma grafting of the plastic material on the expandable stent delivery member. The plastic material also may alternatively be applied by plasma polymerization and deposition of the plastic material on the expandable stent delivery member. In one presently preferred embodiment, the plastic material is selected to adhere or fuse to the expandable stent delivery member. Where the plastic material fuses to the expandable stent delivery member, the plastic material preferably has a lower melt temperature than the expandable stent delivery member. The surface of the expandable stent delivery member may also be etched prior to applying the plastic material to the expandable stent delivery member. In another presently preferred aspect, the thickness of the applied plastic material does not exceed the thickness of the stent.

In an alternate preferred embodiment, the invention provides for a method for retaining a stent on an expandable stent delivery member, the stent having a surface defining a plurality of openings in the stent, wherein the method comprises the steps of mounting the stent over the expandable stent delivery member, and applying a relatively thick solution or dispersion of the plastic material that is insoluble in blood on the expandable stent delivery member through the openings of the stent adjacent to the stent struts. The plastic material on the expandable stent delivery member is then permitted to dry or set, to deposit the plastic material on the expandable stent delivery member, to retain the stent on the expandable stent delivery member. In this embodiment, in addition to the plastic materials mentioned above, the plastic material may also be a two part epoxy resin adhesive, a UV cured plastic material, or the like. In a presently preferred aspect, the step of applying the plastic material comprises forming knobs or fillets on the expandable stent delivery member adjacent to the struts of the stent, and preferably the thickness of the knobs or fillets does not exceed the thickness of the stent. The knobs or fillets serve to retain the stent on the expandable stent delivery member until the stent is deployed by expansion of the expandable stent delivery member, and when the expandable stent delivery member is deflated, after the stent is deployed, the knobs or fillets remain attached to the expandable stent delivery member.

In an alternate preferred embodiment, a stent may be retained on an expandable stent delivery member by mounting the stent over the expandable stent delivery member, melting a plastic material that is insoluble in blood, applying the melted plastic material onto the expandable stent delivery member through the openings of the stent adjacent to the stent struts, and allowing the plastic material to cool, to retain the stent on the expandable stent delivery member. In a presently preferred aspect, the applied melted plastic material forms knobs or fillets on the expandable stent delivery member adjacent to the openings of the stent, and preferably the thickness of the knobs or fillets does not exceed the thickness of the stent. It is desirable that the plastic material have a lower melt temperature than the expandable stent delivery member, in order to avoid damaging the stent delivery member. The plastic material may be of the same class or type of material of which the expandable stent delivery member is made, but having a lower melting temperature, allowing a good bond to be obtained without damaging the expandable stent delivery member. The knobs or fillets serve to retain the stent on the expandable stent delivery member until the stent is deployed by expansion of the expandable stent delivery member, and when the expandable stent delivery member is deflated, after the stent is deployed, the knobs or fillets remain attached to the expandable stent delivery member.

The plastic material may be chosen from plastics, organic materials, resins, two part resins, polymers, and copolymers, and combinations thereof. In a presently preferred embodiment, the plastic material is chosen from EAA copolymers, PVC, ethylene vinyl acetate copolymer (EVA), ethylene glycol butyl ether acetate (EBA) and ethylene methyl acrylate (EMA) ethylene acrylic ester copolymers, ethylene acrylic ester-maleic anhydride terpolymers, and acid copolymer resins.

In another presently preferred embodiment, the present invention provides for a system for applying a melted plastic material that is insoluble in blood on an expandable stent delivery member for retaining a stent on the expandable stent delivery member. The system comprises a holder for positioning the expandable stent delivery member with the stent disposed over the expandable stent delivery member, a microscope system for providing guidance for application of the melted plastic material on the expandable stent delivery member through the openings in the stent, a reservoir for the melted plastic material, and a high pressure controlled piston system connected in fluid communication with the reservoir for receiving the melted plastic material. The high pressure controlled piston system includes a nozzle, and means are provided for controlling the position and motion of the nozzle for dispensing the melted plastic material onto the expandable stent delivery member through the openings of the stent adjacent to the struts of the stent to retain the stent on the expandable stent delivery member.

These and other aspects and advantages of the invention will become apparent from the following detailed description and the accompanying drawings, which illustrate by way of example the features of the invention.

BRIEF DESCRIPTION OF THE DRAWINGS

FIG. 1 is a top plan view of an inflatable stent delivery balloon member illustrating a first embodiment of the method of the invention;

FIG. 2 is a sectional view of a portion of the inflatable stent delivery balloon member of FIG. 1 showing a coating of plastic material on the surface of the inflatable stent delivery balloon member;

FIG. 3 is a top plan view of a stent mounted on the inflatable stent delivery balloon member of FIG. 1;

FIG. 4 is a sectional view of a portion of the stent and inflatable stent delivery balloon member of FIG. 3, showing the coating of plastic material between the stent and inflatable stent delivery balloon member;

FIG. 5 is an end view of a stent, illustrating a variant of the first embodiment of the method of the invention;

FIG. 6A is an enlarged, partial sectional view of a portion of the inflatable stent delivery balloon member taken along line 6—6 of FIG. 5 showing a coating of plastic material on the inner surface of the stent, prior to mounting of the stent on an inflatable stent delivery balloon member;

FIG. 6B is an enlarged, partial sectional view of a portion of the inflatable stent delivery balloon member taken along line 6—6 of FIG. 5 showing a coating of plastic material over the entire surface of the stent, prior to mounting of the stent on an inflatable stent delivery balloon member;

DETAILED DESCRIPTION OF THE PREFERRED EMBODIMENTS

Figure 7:
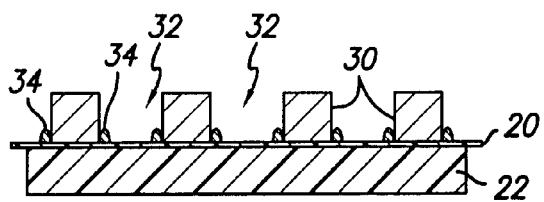
FIG. 7 is a sectional view of a portion of the stent and inflatable stent delivery balloon member of FIG. 3, illustrating a second embodiment of the method of the invention, showing the coating of plastic material forced out from under the stent into openings in the stent adjacent to the stent struts, to retain the stent on the inflatable stent delivery balloon member.

As is illustrated in the drawings, the invention is accordingly embodied in a method for retaining a stent on an expandable stent delivery member. Referring to FIGS. 1–4, in one presently preferred embodiment, a plastic material 20 can be applied to the outer surface of an expandable stent delivery member 22, such as an inflatable balloon member, typically mounted on a stent delivery catheter 24, only a portion of which is illustrated, for purposes of simplicity. A stent 26 having strut members 30 can be mounted on the expandable stent delivery member, as shown in FIG. 3.

The plastic material is preferably insoluble in blood, and may be chosen from plastics, organic materials, resins, two part resins, polymers, and copolymers, combinations thereof, and the like. The plastic material preferably will adhere to the material of the expandable stent delivery member, such as an inflatable stent delivery balloon, and preferably has a relatively high coefficient of friction with the struts of the stent, compared to other, current strut-balloon combinations. A presently preferred plastic material is ethylene acrylic acid (EAA) copolymer, available from Michelman, Inc. under the name "Michem Prime" in the form of dispersions of EAA copolymer resin available from Dow Chemical Co. under the name "Primacor". Presently preferred EAA copolymers from Michelman, Inc. are Michem Prime 4990R (MP4990R), a dispersion of Primacor 5990i, and Michem Prime 4983R (MP4983R), a dispersion of Primacor 5980i. Such EAA copolymers advantageously will adhere to the material of the expandable stent delivery member, such as an inflatable stent delivery balloon. In addition to EAA copolymers, other plastic materials that may also be suitable are polyvinyl chloride (PVC), ethylene vinyl acetate copolymers (EVA), ethylene glycol butyl ether acetate copolymers (EBA, also known as EB Acetate), ethylene methyl acrylate copolymers (EMA), ethylene acrylic ester copolymers, available from ATO Elf Atochem and Exxon Chemical, ethylene acrylic ester-maleic anhydride terpolymers available from ATO Elf Atochem, acid copolymer resins available from DuPont under the name "NUCREL", and combinations thereof. The plastic material may also include one or more cross-linking agents, such as cross-linking catalysts and resins, for example. The plastic material may further comprise a therapeutic agent, such as one or more compatible anti-thrombus agents, one or more drugs for reducing the likelihood of clots forming on the stent and the stent delivery member during exposure of the stent and the stent delivery member to blood, and one or more anti-restenosis agents.

Referring to FIGS. 1 and 2, in a presently preferred embodiment, the expandable stent delivery member 22 is provided with a thin coating of the adhesive plastic material 20 on the outer surface of the expandable stent delivery member, by dissolving the plastic material in a solvent to form a dispersion of the plastic material, and then applying the plastic material, by dipping the expandable stent delivery member in the dispersion of plastic material. The plastic material may also be applied by other suitable methods, such as by brushing, spraying or other similar conventional application methods. One currently preferred solvent, for a Primacor dispersion, comprises a mixture of water and ammonia, brought to a pH of about 9. The solvent mixture may also include other solvents, such as isopropyl alcohol, for example, to improve surface characteristics of the dispersion in solution.

Alternatively, or in addition to the thin coating of adhesive plastic material on the expandable stent delivery member, as is illustrated in FIGS. 5 and 6A, the inner surface of the stent 26 may be provided with a thin coating 28 of adhesive plastic material prior to mounting of the stent on the expandable stent delivery member, such as by brushing, dipping, spraying or other similar conventional application methods. As is illustrated in FIGS. 5 and 6B, substantially the entire surface of the stent 26 may be provided with a thin coating 28 of adhesive plastic material prior to mounting of the stent on the expandable stent delivery member, such as by dipping the stent, although the entire stent may be coated by brushing, spraying or other similar conventional application methods. The surface of the expandable stent delivery member may also be etched prior to application of the plastic material, to improve adherence of the plastic material to the expandable stent delivery member, and areas of the expandable stent delivery member may be masked prior to etching the surface of the expandable stent delivery member, so as to limit areas of improved adherence. When the expandable stent delivery member is an inflatable stent delivery balloon member, the balloon member is preferably folded prior to the application of the dispersion of the plastic material on the balloon member, as is indicated by fold line 29, so that the dispersion of plastic material is only applied on the outer edges of the folds of the balloon member, to form a thin coating in the stent mounting area, to further limit any possible interference of the plastic material with the inflation of the balloon member or the release of the stent upon inflation of the balloon. The solvent is then evaporated from the coating of the dispersion of the plastic material on the expandable stent delivery member to deposit the plastic material on the expandable stent delivery member, such as by allowing the dispersion to air dry under ambient conditions, or by the application of heat, air circulation and/or a lowered pressure, for example.

Thereafter, as is illustrated in FIGS. 3 and 4, the stent 26 is mounted on the expandable stent delivery member by disposing the stent over the expandable stent delivery member 22 and crimping the stent over the expandable stent delivery member by the application of pressure and/or heat to the stent over the expandable stent delivery member. The stent is preferably crimped over the expandable stent delivery member by rolling the assembly of the stent and the expandable stent delivery member between two resilient plates under a controlled pressure, to press the stent struts against the expandable stent delivery member. This process may be modified by heating the plates to a controlled temperature, or by blowing heated air between the plates. The application of heat and pressure to the stent and the expandable stent delivery member may improve the creation of an adhesive bond of the plastic material to the expandable stent delivery member, and may also improve adherence of the plastic material between the expandable stent delivery member and the stent. Optionally in addition to application of heat and pressure, the expandable stent delivery member may also be partially inflated to assist in seating of the stent on the expandable stent delivery member.

In a second embodiment of the method of the invention, illustrated in FIG. 7, a plastic material 20 is selected that will deform under heat and/or pressure, so that following the step of applying the coating to the expandable stent delivery member 22, applying the coating to the stent 26, or both, as described above, in crimping the stent into place in a normal manner as described above, the mounting of the stent to the expandable stent delivery member will force some of the plastic material from beneath the strut members 30 of the stent into openings 32 between the strut members of the stent and adjacent to the strut members of the stent, to form ridges, ribs or fillets 34 to thus increase the stent retention properties of the plastic material on the expandable stent delivery member, to retain the stent on the inflatable stent delivery balloon member. In this case, a plastic material is preferred that would deform under temperatures and/or pressures applied that would not significantly damage the expandable stent delivery member. With some plastic material, the crimping pressure will be enough to create an adhesive bond and/or displace the coating under the stent struts to form the ridges, ribs or fillets of plastic material to thus increase the stent retention properties of the plastic material on the expandable stent delivery member. In some cases, both heat and pressure may need to be applied to create adequate adhesion and/or deformation of the plastic coating. Deformation or displacement of the coating under the stent struts advantageously avoids adding all of the coating's thickness to the crossing profile of the stent. Ideally, the thickness of the coating of the applied plastic, whether deformed or not deformed, should not exceed that of the stent. For example, for a stent with struts that are approximately 0.003 inch thick, the thickness of the coating of the applied plastic, whether deformed or not deformed, should be no greater than about 0.003 inch thick.

If the adhesive or friction force is too high, the stent may not completely release from the expandable stent delivery member after the expandable stent delivery member is expanded, and the stent struts may be unevenly expanded or even pulled apart. Uneven stent expansion can result in areas of the vasculature being inadequately scaffolded by the deployed stent. In cases where the method of application or plastic material selected results in too great an adhesive or friction force, and too great a retentive force on the stent, a release agent may also be applied to the stent, the expandable stent delivery member, or both, prior to the mounting of the stent over the expandable stent delivery member, to help ensure that some plastic material doesn't remain attached to the stent after deployment of the stent. Heat may also be applied to the stent mounted over the expandable stent delivery member to accelerate or initiate cross-linking of the plastic material.

Figure 8:
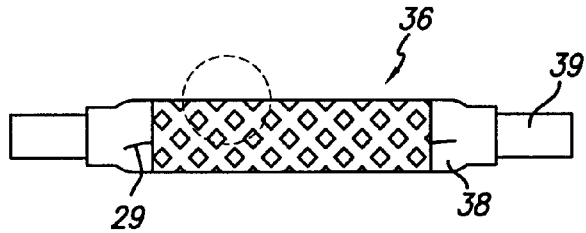
FIG. 8 is a top plan view of a stent mounted on an inflatable stent delivery balloon member, illustrating a third embodiment of the method of the invention.
Figure 9:
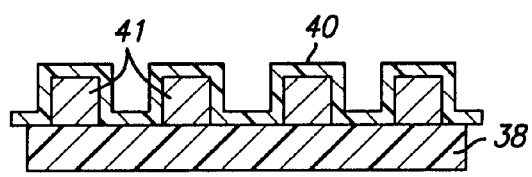
FIG. 9 is a sectional view of a portion of the stent and inflatable stent delivery balloon member of FIG. 8, showing a coating of plastic material on the surface of the inflatable stent delivery balloon member and on the surface of the stent.

Alternatively, as is illustrated in FIGS. 8 and 9, the stent 36 can be mounted on the expandable stent delivery member 38 of a stent delivery catheter 39 prior to application of the plastic material, so that the dispersion of plastic material is applied to both of the expandable stent delivery member and the stent to form a thin coating 40 of the dispersion of the plastic material on the expandable stent delivery member and the struts 41 of the stent, shown in FIG. 9, after which the solvent is then evaporated from the coating of the dispersion of the plastic material on the expandable stent delivery member to deposit the plastic material on the expandable stent delivery member, as described above. In either case, the thickness of the coating of the plastic material can be adjusted by selecting the dilution of the dispersion as desired, and preferably, the thickness of the coating is controlled by adjusting the dilution of the dispersion to be sufficiently thin so as to not significantly interfere with subsequent inflation of the expandable stent delivery member and deployment of the stent. In a presently preferred embodiment, the thickness of the applied plastic material once it has been deposited and evaporated to dryness does not exceed the thickness of the stent. In addition, when the expandable stent delivery member is an inflatable stent delivery balloon and is folded prior to application of the dispersion of plastic material, the coating of the plastic material may cover the edges of the folds of the balloon, but should not bond the folds of the balloon together.

Figure 10:
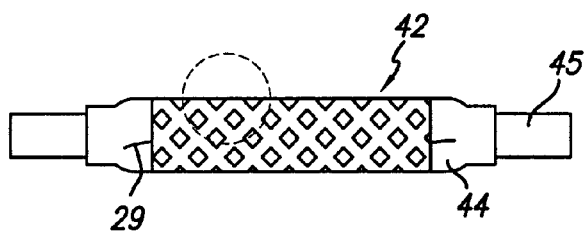
FIG. 10 is a top plan view of a stent mounted on an inflatable stent delivery balloon member, illustrating a fourth embodiment of the method of the invention.
Figure 11:
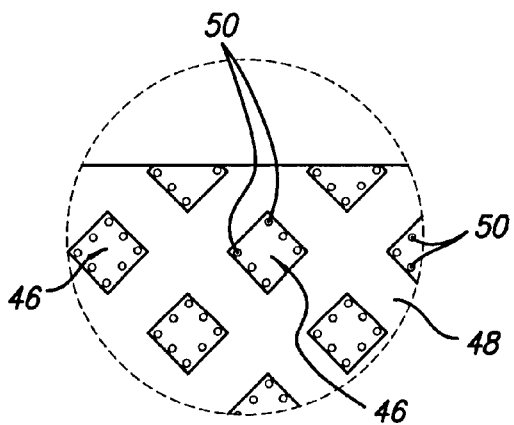
FIG. 11 is an enlarged view of a portion of the stent and inflatable stent delivery balloon member of FIG. 10, showing the application of knobs of plastic material on the inflatable stent delivery balloon member through openings in the stent adjacent to the stent struts, to retain the stent on the inflatable stent delivery balloon member.
Figure 12:
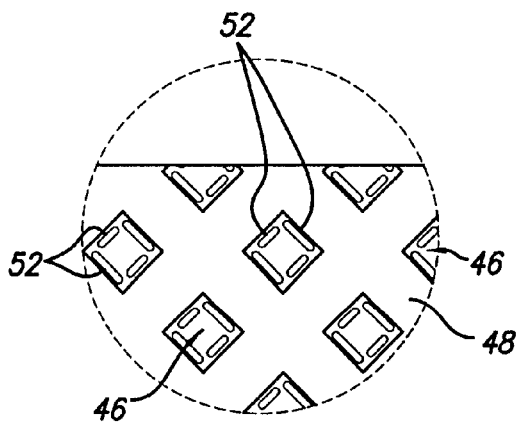
FIG. 12 is an enlarged view of a portion of the stent and inflatable stent delivery balloon member of FIG. 10, showing the application of fillets of plastic material on the inflatable stent delivery balloon member through openings in the stent adjacent to the struts, to retain the stent on the inflatable stent delivery balloon member.

As is illustrated in FIGS. 10–12, a relatively thick solution or dispersion of the plastic material that is insoluble in blood can be applied on the expandable stent delivery member 44 through the openings 46 of the stent 42 adjacent to the stent struts 48, in the shape of knobs 50 shown in FIG. 11, and/or fillets or ridges 52 shown in FIG. 12, by brushing, or by a syringe or the like. The plastic material is then allowed to dry or set on the expandable stent delivery member, to deposit the plastic material on the expandable stent delivery member, to retain the stent on the expandable stent delivery member. The application of heat to dry or facilitate curing of the plastic material is optional. The thickness of the knobs or fillets preferably does not exceed the thickness of the stent. In addition to the plastic materials discussed above, the plastic material may also be a two part epoxy resin adhesive, a UV cured plastic material, or the like. The knobs or fillets serve to retain the stent on the expandable stent delivery member until the stent is deployed by expansion of the expandable stent delivery member, and when the expandable stent delivery member is deflated, after the stent is deployed, the knobs or fillets remain attached to the expandable stent delivery member.

EXAMPLE 1

Plasma Etch Folded Balloon/Stent. A stent was crimped over a stent delivery balloon, both of which were obtained from Advanced Cardiovascular Systems under the name "DUET." The balloon was etched in a plasma chamber, with the stent acting as a mask and holding the balloon folded tightly during etching, in order to make the solution of plastic material wet the surface of the balloon and adhere better to the surface of the balloon. A solution of plastic material, a 50/50 by volume mixture of MP 4990R (EAA, Primacor dispersion) and a pH about 9, ammonia and water mixture, was prepared. The stent was then removed from the balloon, and the solution of plastic material was brushed thinly onto the balloon's stent area. The solution provided a thin coating, not visible to the naked eye, over the etched areas, without wicking to the balloon folds, and was allowed to air dry for a minute or two. After expanding the stent slightly to replace the stent over the balloon, the stent was then crimped onto the balloon, under a pressure of about 20 p.s.i. by wrapping the stent over the balloon tightly with Teflon tape, and at a temperature of about 200° F., and unwrapping the stent and balloon afterwards. A physician evaluating the mounting of the stent on the balloon was unable to remove the stent from the balloon. The physician also reported that the stent subsequently deployed normally at a normal balloon inflation pressure of about 7 atm., with no coating or debris visible on either the stent or the balloon.

EXAMPLE 2

A comparison test was carried out, by preparing five test stents crimped over 3.0×18 mm Advanced Cardiovascular Systems Multi-Link Tetra catheter stent delivery balloons. The balloons were tri-folded, wiped with alcohol, and placed in a plasma theater to etch the balloons. A plastic material mixture of 250 cc of distilled water, 1 cc of ammonia, and 0.5 cc of a Primacor dispersion (MP 4990R) was prepared. The plastic material mixture was applied on the tri-folded balloons using a micro-brush, and was allowed to dry on the balloons overnight. The stents were then mounted over the balloons by sliding the stents over the balloons, and preliminarily crimping the stents on the balloons using a roll crimper. Protective Teflon sheaths were placed over the stents, and a grip machine was used to further crimp the stents, at a temperature of about 200° F., and under a pressure of about 100 p.s.i., after which the protective sheaths were removed. Five control stents were similarly crimped over a Multi-Link Tetra catheter stent delivery balloon 3.0×18 mm. without any plastic material mixture applied over the balloon. Tensile pull tests were performed on the mounted control and test stents, to determine the force required to remove the stents from the stent delivery balloons, with the results shown in Table 1 below. It is readily apparent from the test results that the test stents were retained on the stent delivery balloons much more strongly than the control stents were, and on average were retained roughly twice as strongly as the control stents were.

TABLE 1

| Samples | Control Removal Force (lbf.) | Test Removal Force (lbf.) |
| --- | --- | --- |
| 1 | 0.512 | 1.403 |
| 2 | 0.117 | 1.545 |
| 3 | 0.776 | 1.505 |
| 4 | 0.620 | 1.199 |
| 5 | 0.705 | 1.989 |
| Averages | 0.746 | 1.528 |

Referring to FIGS. 10–13, in a preferred alternate embodiment, a plastic material is selected which will adhere and/or fuse to the balloon material, and that preferably has a lower melt temperature than the balloon material. The plastic material is preferably insoluble in blood, and may be chosen from plastics, organic materials, resins, two part resins, polymers, and copolymers, combinations thereof, and the like. The plastic material preferably has a relatively high coefficient of friction with the struts of the stent, compared to other, current strut-balloon combinations. A presently preferred plastic material is ethylene acrylic acid (EAA) copolymer, that will adhere to the material of the expandable stent delivery member, such as an inflatable stent delivery balloon. In addition to EAA copolymers, other plastic materials that may also be suitable include polyvinyl chloride (PVC), ethylene vinyl acetate copolymers (EVA), ethylene glycol butyl ether acetate copolymers (EBA, also known as EB Acetate), ethylene methyl acrylate copolymers (EMA), ethylene acrylic ester copolymers, available from ATO Elf Atochem and Exxon Chemical, ethylene acrylic ester-maleic anhydride terpolymers available from ATO Elf Atochem, and acid copolymer resins available from DuPont under the name "NUCREL", and combinations thereof. The plastic material may also include one or more cross-linking agents or cross-linking catalysts, such as azobisisobutronitrile for example, and resins or monomers, for example. The plastic material may further comprise a therapeutic agent, such as one or more compatible anti-thrombus agents, one or more drugs for reducing the likelihood of clots forming on the stent and the stent delivery member during exposure of the stent and the stent delivery member to blood, and one or more anti-restenosis agents. Preferred examples of therapeutic agents or pharmacologic compounds include taxol, aspirin, prostaglandins, antiplatelets, antithrombins, cytostatic or antiproliferative agents, sodium heparin, low molecular weight heparin, hirudin, argatroban, forskolin, vapiprost, prostacyclin and prostacyclin analogues, dextran, D-phe-pro-arg-chloromethylketone, dipyridamole, glycoprotein IIb/IIIa platelet membrane receptor antibody, recombinant hirudin, thrombin inhibitor, angiopeptin, angiotensin converting enzyme inhibitors, Lisinopril, and cisplatin; anti-inflammatories such as steroids; anti-cancer compounds such as taxon and actinomycin; macromolecules such as peptides, proteins, genes and antisense compounds; calcium channel blockers, colchicine, fibroblast growth factor antagonists, fish oil, omega 3-fatty acid, histamine antagonists, HMG-CoA reductase inhibitor, methotrexate, monoclonal antibodies, nitroprusside, phosphodiesterase inhibitors, prostaglandin inhibitor, serotonin blockers, thio-protease inhibitors, triazolopyrimidine and other PDGF antagonists, alpha-interferon and genetically engineered epithelial cells, supramolecular weight structures with molecular weights greater than 100,000 daltons, and up to about 1,000,000 daltons, including viral particles used for gene therapy, ribozymes and liposomes, and combinations thereof.

Figure 13:
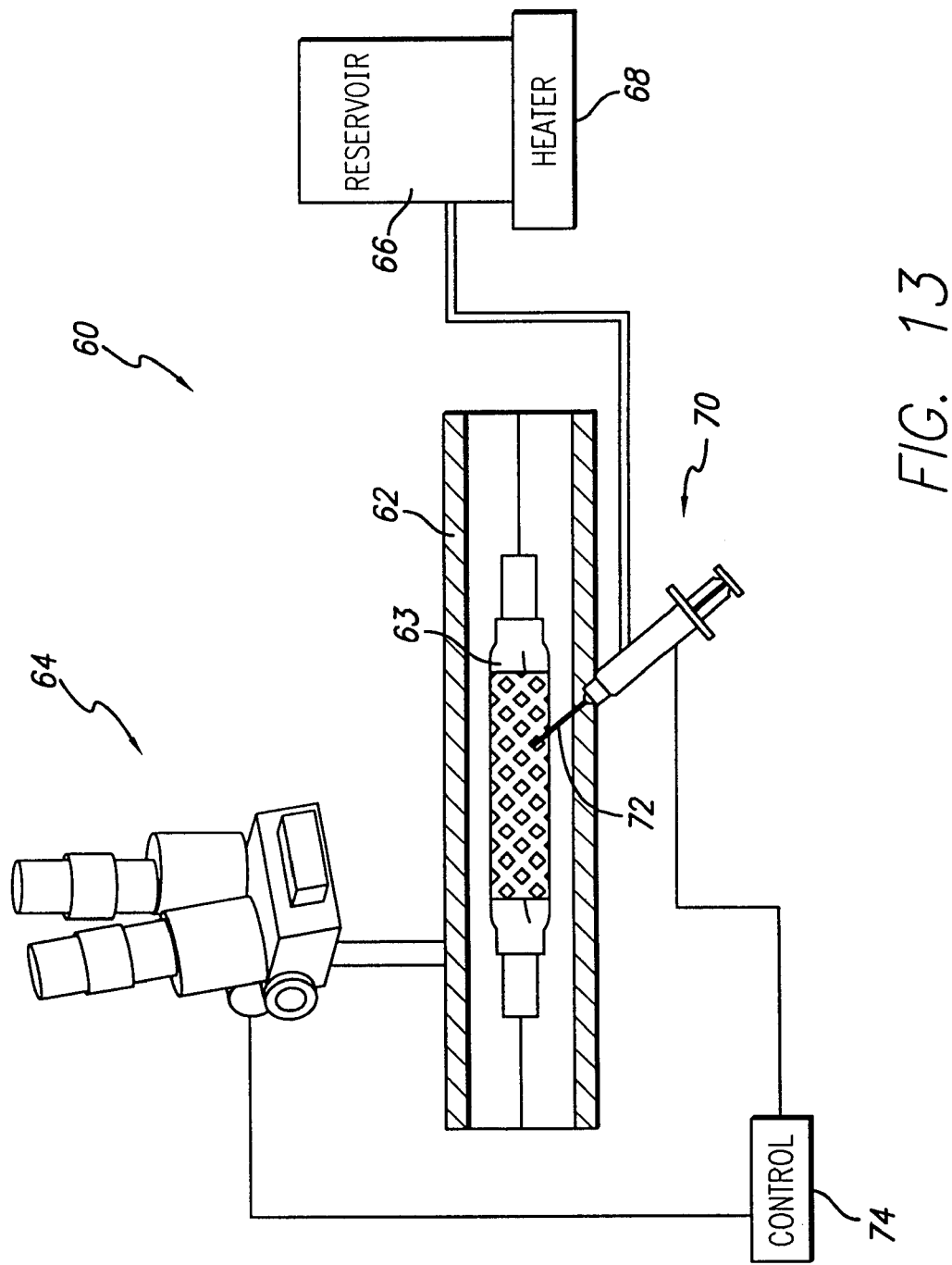
FIG. 13 is a schematic diagram of a system for applying a melted plastic material that is insoluble in blood on an expandable stent delivery member for retaining a stent on the expandable stent delivery member.

In this alternate embodiment of the method for retaining a stent on an expandable stent delivery member, the method generally involves the steps of mounting the stent 42 over the expandable stent delivery member 44 of the stent delivery catheter 45, melting a selected plastic material that is insoluble in blood, and applying small dabs of the melted plastic material onto the expandable stent delivery member, such as a stent delivery balloon, through the openings 46 between the struts 48 of the stent adjacent to the stent struts to form knobs 50 shown in FIG. 11, and/or fillets or ridges 52 shown in FIG. 12, on the expandable stent delivery member adjacent to the stent struts. The melted plastic material can be applied, for example, by a system 60 such as is illustrated in FIG. 13. In a presently preferred embodiment, the thickness of the knobs and/or fillets does not exceed the thickness of the stent. The plastic material is then allowed to cool, to retain the stent on the expandable stent delivery member until the stent is deployed by expansion of the expandable stent delivery member. Ideally, when the expandable stent delivery member is deflated, after the stent is deployed, the knobs and/or fillets will remain attached to the expandable stent delivery member.

Optionally, as noted above, a release agent can be applied to one or both of the stent and the expandable stent delivery member prior to the step of mounting the stent over the expandable stent delivery member, to facilitate release of the stent from the expandable stent delivery member when the expandable stent delivery member is to be inflated to deploy the stent. The release agent is preferably biocompatible, such as a silicone oil, or a fluorocarbon polymer such as a powdered tetrafluoroethylene that can be sprayed on, although other biocompatible polymeric release agents may also be suitable. In another presently preferred optional step, the surface of the expandable stent delivery member can be etched prior to applying the melted plastic material to the expandable stent delivery member. As noted above, etching can be performed in a plasma chamber, or by application of a chemical etching agent such as methylene chloride or acids, for example.

A plastic application system 60 that can be used to apply the melted plastic material in a rapid manner is illustrated in FIG. 13. The system generally includes a holder 62 for positioning the expandable stent delivery member 63 with the stent disposed over the expandable stent delivery member, and a microscope system 64 for providing guidance for applying the melted plastic material on the expandable stent delivery member through the openings in the stent adjacent to the struts of the stent. A reservoir 66, typically having an associated heater 68, is provided for supplying melted plastic material to a high pressure controlled piston syringe 70 having a nozzle 72, and a control unit 74 is provided for controlling the position and motion of the nozzle, for dispensing the melted plastic material onto the expandable stent delivery member as knobs or fillets as desired, to retain the stent on the expandable stent delivery member.

Ideally, after position information is input from the microscope system to the control unit, the nozzle tip would be rapidly positioned over the expandable stent delivery member between the stent struts, would squirt out a metered amount of melted plastic, and would rapidly move away from the expandable stent delivery member. This would be repeated for each application location. Preferably the time the nozzle is near the balloon would be minimized, to minimize the heating of the balloon and thus any chance that the balloon would be damaged. Ideally, the height of the knobs and/or fillets should not exceed that of the stent. The applied knobs or fillets will mechanically interfere with movement of the stent distally or proximally in response to forces generated in positioning the stent for deployment. Additionally, the knobs or fillets of plastic material may adhere to the stent, if the plastic material is selected to adhere to the stent material, to facilitate retention of the stent on the expandable stent delivery member until the stent is deployed by inflation of the expandable stent delivery member. When the expandable stent delivery member is deflated, after stent deployment, these knobs and/or fillets will remain attached to the expandable stent delivery member. Plasma or chemical etching of the surface of the expandable stent delivery member prior to the application of the knobs and/or fillets may enhance this attachment. In the case of an adhesive plastic material, a release agent could be applied to the stent to help ensure that some plastic would not remain attached to the stent after deployment, if necessary.

It will be apparent from the foregoing that while particular forms of the invention have been illustrated and described, various modifications can be made without departing from the scope of the invention. Accordingly, it is not intended that the invention be limited, except as by the appended claims.

What is claimed is:

1. A method for retaining a stent on an expandable stent delivery member, the stent including a plurality of struts and openings defined in the surface of the stent between the struts, comprising the steps of:

applying a plastic material that is insoluble in blood to at least one of the expandable stent delivery member and the stent; and mounting the stent over the expandable stent delivery member by disposing the stent on the expandable stent delivery member, and applying heat and pressure to the stent and the expandable stent delivery member to form ridges of plastic material in the openings of the stent adjacent to the struts, to retain the stent on the expandable stent delivery member.

2. The method of claim 1, wherein the plastic material is selected from the group consisting of plastics, organic materials, resins, two part resins, a UV cured plastic material, polymers, and copolymers, and combinations thereof.

3. The method of claim 1, wherein the plastic material is selected from the group consisting of ethylene acrylic acid, polyvinyl chloride, ethylene vinyl acetate copolymers, ethylene glycol butyl ether acetate copolymers, ethylene methyl acrylate copolymers, ethylene acrylic ester copolymers, ethylene acrylic ester-maleic anhydride terpolymers, and acid copolymer resins.

4. The method of claim 1, wherein the plastic material further comprises a therapeutic agent selected from the group consisting of compatible anti-thrombus agents and drugs for reducing the likelihood of clots forming on the stent and the stent delivery member during exposure of the stent and the stent delivery member to blood.

5. The method of claim 1, wherein the plastic material further comprises an anti-restenosis agent.

6. The method of claim 1, wherein the plastic material further comprises a cross-linking agent selected from the group consisting of cross-linking catalysts and resins.

7. The method of claim 1, wherein the plastic material will adhere to the expandable stent delivery member.

8. The method of claim 7, wherein the step of mounting the stent over the expandable stent delivery member creates an adhesive bond between the stent and the expandable stent delivery member.

9. The method of claim 1, wherein the step of applying the plastic material comprises dissolving the plastic material in a solvent to form a dispersion and applying the dispersion of the plastic material to the expandable stent delivery member, and further comprising the step of evaporating the solvent from the dispersion of the plastic material on the expandable stent delivery member to deposit the plastic material on the expandable stent delivery member.

10. The method of claim 9, further comprising the step of folding the expandable stent delivery member prior to applying the dispersion of the plastic material on the expandable stent delivery member.

11. The method of claim 1, wherein the step of dissolving the plastic material in a solvent to form a dispersion comprises adjusting the dilution of the dispersion to control the thickness of the coating.

12. The method of claim 11, wherein the thickness of the applied plastic material does not exceed the thickness of the stent.

13. The method of claim 9, wherein the step of dissolving the plastic material in a solvent to form a dispersion comprises adjusting the dilution of the dispersion to be sufficiently thin so as to not significantly interfere with subsequent inflation of the expandable stent delivery member and deployment of the stent.

14. The method of claim 1, wherein the step of applying the plastic material comprises dissolving the plastic material in a solvent to form a dispersion, folding the expandable stent delivery member, and applying the dispersion of the plastic material on the expandable stent delivery member prior to the step of mounting the stent to the expandable stent delivery member, to form a thin coating of the dispersion of the plastic material on the expandable stent delivery member.

15. The method of claim 1, wherein the step of applying the plastic material comprises dissolving the plastic material in a solvent to form a dispersion, mounting the stent on the expandable stent delivery member, and applying the dispersion of the plastic material on the expandable stent delivery member and the stent to form a thin coating of the dispersion of the plastic material on the expandable stent delivery member and the stent.

16. The method of claim 1, wherein the expandable stent delivery member is an inflatable balloon member.

17. The method of claim 1, wherein the step of applying the plastic material comprises applying the plastic material by plasma grafting of the plastic material on the expandable stent delivery member.

18. The method of claim 1, wherein the step of applying the plastic material comprises applying the plastic material by plasma polymerization and deposition of the plastic material on the expandable stent delivery member.

* * * * *

UNITED STATES PATENT AND TRADEMARK OFFICE
CERTIFICATE OF CORRECTION

PATENT NO. : 6,682,553 B1
DATED : January 27, 2004
INVENTOR(S) : William E. Webler, Jr.

It is certified that error appears in the above-identified patent and that said Letters Patent is hereby corrected as shown below:

<u>Column 13,</u>
Line 32, delete "claim 1" and insert -- claim 9 --.

Signed and Sealed this

Twentieth Day of July, 2004

JON W. DUDAS
*Acting Director of the United States Patent and Trademark Office*